(12) United States Patent
Montagu

(10) Patent No.: US 6,984,828 B2
(45) Date of Patent: *Jan. 10, 2006

(54) QUANTIFIED FLUORESCENCE MICROSCOPY

(76) Inventor: Jean I. Montagu, 76 Walnut Pl., Brookline, MA (US) 02445-6750

( * ) Notice: Subject to any disclaimer, the term of this patent is extended or adjusted under 35 U.S.C. 154(b) by 0 days.

This patent is subject to a terminal disclaimer.

(21) Appl. No.: 10/214,221

(22) Filed: Aug. 7, 2002

(65) Prior Publication Data

US 2003/0015668 A1   Jan. 23, 2003

Related U.S. Application Data

(63) Continuation of application No. PCT/US01/04336, filed on Feb. 9, 2001, and a continuation-in-part of application No. 09/500,626, filed on Feb. 9, 2000, now Pat. No. 6,472,671.

(51) Int. Cl.
G12B 13/00   (2006.01)

(52) U.S. Cl. ............ 250/458.1; 378/44; 356/213; 600/477

(58) Field of Classification Search ............ 250/458.1; 378/44; 356/213; 600/477
See application file for complete search history.

(56) References Cited

U.S. PATENT DOCUMENTS

| | | | |
|---|---|---|---|
| 4,735,877 A | 4/1988 | Kato et al. | 430/5 |
| 4,861,144 A | 8/1989 | Russell | 350/412 |
| 4,886,968 A | 12/1989 | Ohnishi et al. | 250/327 |
| 4,980,114 A | 12/1990 | Satake et al. | 264/288.4 |
| 4,981,783 A | 1/1991 | Augenlicht | 435/6 |
| 5,091,652 A | 2/1992 | Mathies et al. | 250/458 |
| 5,216,247 A | 6/1993 | Wang et al. | 369/97 |
| 5,224,240 A | 7/1993 | Smith et al. | 369/97 |
| 5,262,128 A | 11/1993 | Leighton et al. | 422/100 |
| 5,274,240 A | 12/1993 | Mathies et al. | 250/458 |
| 5,293,363 A | 3/1994 | Takeshita | 369/44 |
| 5,315,375 A | 5/1994 | Allen | 356/417 |
| 5,381,224 A | 1/1995 | Dixon et al. | 356/72 |
| 5,424,186 A | 6/1995 | Fodor et al. | 435/6 |
| 5,424,841 A | 6/1995 | Van Gelder et al. | 356/417 |

(Continued)

FOREIGN PATENT DOCUMENTS

WO   WO 99/00689   7/1999

(Continued)

OTHER PUBLICATIONS

Alexay, C. et al; Fluorescence Scanner Employing a Macro Scanning Objective; SPIE vol. 2705 pp. 63-72, 1996.

(Continued)

Primary Examiner—Otilia Gabor
Assistant Examiner—Christine Sung
(74) Attorney, Agent, or Firm—William McCarthy, III; Philip L. McGarrigle; Ivan David Zitkovsky

(57) ABSTRACT

The present invention relates to calibration apparatuses, methods or tools used in microscopy. A calibration tool for fluorescent microscopy includes a support, a solid surface layer including a fluorescent material, and a thin opaque mask of non-fluorescent material defining reference feature openings having selected dimensions exposing portions of the surface layer. A first type of the calibration tool may include an adhesion promoter facilitating contact between the surface of the support and the solid surface layer including the fluorescent material, which is in contact with the thin opaque mask. A second type of the calibration tool may include the thin opaque mask fabricated (with or without an adhesion promoter) onto the support, and the solid surface layer including the fluorescent material located on the thin opaque mask.

42 Claims, 9 Drawing Sheets

U.S. PATENT DOCUMENTS

| | | | |
|---|---|---|---|
| 5,459,325 A | 10/1995 | Hueton et al. | 250/458 |
| 5,578,832 A | 11/1996 | Trulson et al. | 250/458 |
| 5,585,639 A | 12/1996 | Dorsel et al. | 250/458 |
| 5,610,754 A | 3/1997 | Gheen et al. | 359/210 |
| 5,631,734 A | 5/1997 | Stern et al. | 356/317 |
| 5,646,411 A | 7/1997 | Kain et al. | 250/458 |
| 5,672,880 A | 9/1997 | Kain | 250/458 |
| 5,719,391 A | 2/1998 | Kain | 250/235 |
| 5,721,435 A | 2/1998 | Troll | |
| 5,737,121 A | 4/1998 | Dixon | 359/388 |
| 5,760,951 A | 6/1998 | Dixon et al. | 359/385 |
| 5,800,992 A | 9/1998 | Fodor et al. | 435/6 |
| 5,810,930 A * | 9/1998 | Eom et al. | 118/719 |
| 5,880,465 A | 3/1999 | Boettner et al. | 250/234 |
| 5,895,915 A | 4/1999 | DeWeerd et al. | 250/234 |
| 5,910,390 A | 6/1999 | Hatanaka et al. | 430/139 |
| 6,069,984 A | 5/2000 | Sadler et al. | |
| 6,075,613 A | 6/2000 | Schermer et al. | 356/446 |
| 6,157,402 A * | 12/2000 | Torgeson | 348/59 |
| 6,201,639 B1 * | 3/2001 | Overbeck | 359/368 |
| 6,207,960 B1 | 3/2001 | Stern | 250/458 |
| 6,355,934 B1 | 3/2002 | Osgood et al. | |
| 6,381,013 B1 * | 4/2002 | Richardson | 356/305 |
| 6,383,412 B1 * | 5/2002 | Hasegawa | 252/301.4 H |
| 6,631,147 B2 * | 10/2003 | Taniguchi et al. | 372/39 |
| 2002/0028322 A1 * | 3/2002 | Yasuda et al. | 428/210 |
| 2002/0133080 A1 * | 9/2002 | Apruzzese et al. | 600/477 |
| 2003/0105195 A1 * | 6/2003 | Holcomb et al. | 524/102 |

FOREIGN PATENT DOCUMENTS

| | | |
|---|---|---|
| WO | WO 99/36760 | 7/1999 |

OTHER PUBLICATIONS

Mace, Myles L., Jr., et al; Novel Microarray Printing and Detection Technologies; Microarray Biochip Technology, 2000 Bio Techniques Books, Natick, MA.

Patent Abstracts of Japan; vol. 1998, No. 11, Sep. 30, 1998 & JP 10 153529 A (Bunshi Baiohotonikusu Kenkyusho: KK), Jun. 9, 1998 abstract.

Patent Abstract of Japan; vol. 1997, No. 12, Dec. 25, 1997 & JP 09 203865 A (Nikon Corp), Aug. 5, 1997 abstract.

International Search Report dated Dec. 12, 2001, in PCT Application PCT/US01/04336.

* cited by examiner

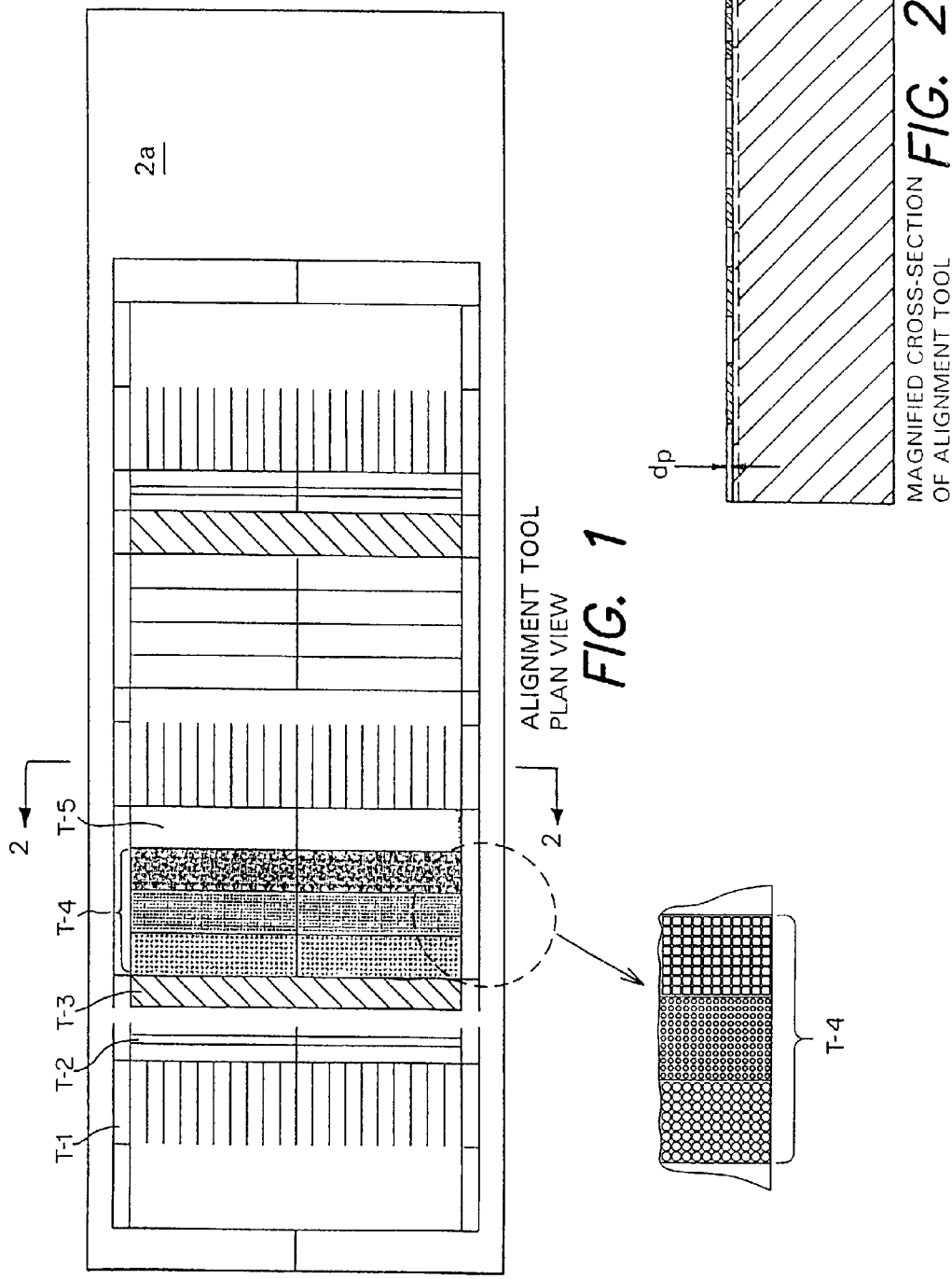

QUANTIFIED FLUORESCENCE MICROSCOPY

This application is a continuation of co-pending PCT Application PCT/US01/04336, filed on Feb. 9, 2001, and is a continuation-in-part of U.S. patent application Ser. No. 09/500,626, filed on Feb. 9, 2000, now U.S. Pat. No. 6,472,671. The disclosure of the above-mentioned applications is considered part of, and is incorporated by reference in the disclosure of this application.

TECHNICAL FIELD

This invention relates to microscopy and more particularly to calibrating a position of a sample with respect to optical elements of a microscope and/or to calibrating fluorescence detection in microscopes.

BACKGROUND

Testing or calibration targets are employed to evaluate system performance of conventional microscopes. These are used to establish a baseline between different microscope systems and to characterize image quality in terms of its conventional components: resolution, contrast, depth of field and distortion. Common offerings for conventional microscopy are the USAF Field Resolution target, the USAF Contrast Resolution Target, the Star Target, the Ronchi Ruling Targets, Modulation Transfer Function Targets, Depth of Field Targets, and Distortion and Aberration Targets. There are others.

The targets are typically printed or vapor deposited patterns on plastic or glass substrates. The optical features on the target are preferably finer than the resolution of the optical system being tested. While it is desirable that the reference features have dimensions or parameters an order of magnitude smaller than those of the specimens to be examined by the microscope, practitioners have had to accept reference dimensions or parameters only 4 or 5 times smaller than those of the specimens to be examined.

Fluorescent microscopy of specimens is different from and more demanding than conventional microscopy because it is based on relatively low-level fluorescent emissions excited by illumination of the specimen, typically employing confocal arrangements for detecting the relatively weak signal through a pin hole or the like. An example is the detection of fluorescence from dried liquid spots containing possibly fluorescing biological material, the dried spots being essentially at the focal plane of the instrument (dried spot thickness less than a few microns). Another example is fluorescence from a biological microarray such as from a GeneChip® biological array product, as produced by Affymetrix, Inc., in which the fluorescing material is of relatively insignificant thickness.

For testing or calibration targets for fluorescence microscopy, besides the numerous conventional components of image quality, there is the requirement of testing the optical efficiency of the system in respect of fluorescence emission. This introduces significant complications, as fluorescence involves an excited photochemical effect, to produce a voltage or signal level in the detector, that introduces signal to noise ratio considerations that interact with measurements of the various optical components involved in the calibration. In general the signal to noise ratio must be at least 3 to 1 to obtain satisfactory operation.

It has been an unsolved problem, to find a calibration target that adequately simulates the fluorescent activity which it is desired to quantify over a broad range of instruments and conditions of use. It is wished to simulate fluorescing specimens that generally lie within the depth of field of the microscope, and in the case of micro dots of biological material, lie essentially at a plane, e.g. in a depth of only a few microns or even substantially less. As the dimensions of individual specimens to be imaged become increasingly smaller as microarray technology advances, the significance of not having a suitable calibration tool has become increasingly severe.

The difficulties for fluorescent microscopy is that, without the desired degree of calibration, it becomes difficult to compare the results obtained in biological or other research performed with different instruments, thus creating serious difficulties in comparing and coordinating the results of different laboratories, whether the laboratories be at different institutions, or separate laboratory facilities within the same institution. Likewise, even with a given instrument, the uncertainties of calibration can introduce errors in the measurement of important actions such as proportional expression, etc. In particular the lack of good reference and calibration is felt at the forefront of research where results are so new and there has been insufficient time or experience to generate reliable standards. The development of true quantified fluorescence microscopy can fulfill this need. On the other hand, the availability of a strong calibration tool will likely to open the possibilities of inexpensive and reliable fluoresence instrumentation and procedures for the clinical setting for diagnosis and treatment. Existing calibration tools for conventional microscopy do not satisfactorily fill the needs of fluorescence microscopy. A number of special techniques have been offered.

One technique, offered by Max Levy Reprographics, uses a layer of organic fluorescent material e.g. of 3 micron thickness, having fluorescence emission across a broad wavelength spectrum, deposited on a non-fluorescent glass substrate such as synthetic quartz. A suitable pattern is then etched away into the fluorescent material, so that the critical edges of the reference are defined by the exposed edges of the fluorescing material. One shortcoming of this technology is that the minimum thickness of the fluorescent material that can be deposited is of the order of 3 micron and, with such thickness, the edges of the pattern do not etch squarely. The finest reference details that can be formed in this material are believed to be approximately 4 micron width lines, spaced apart 8 microns on center. This is unsatisfactory for calibration with respect to instruments employing conventional 5 micron spot size and is an order of magnitude greater than required to evaluate optical spots that are ½ micron in diameter, achievable with a microscope having an 0.7 NA objective in air, or ¼ micron diameter achievable with a 1.4 NA, oil immersion objective. The relatively large thickness of the fluorescent layer poses problems of edge definition, particularly because the fluorescent rays emit at acute angles to the surface and can be blocked by the edges of the material, or on the other hand, the edges themselves fluoresce, to produce confusion.

Another technique for testing a fluorescent microscope uses as a substrate a fluorescent glass on which is deposited a very thin metal layer e.g. a few hundred Angstrom thick. Preferably a nickel layer is employed. A suitable pattern is subsequently etched in the metal to create fine features, as small as ½ micron dimension. Whereas this technique does not have the foregoing edge problem, I have realized that there are shortcomings to this approach, owing to the fact that the glass constitutes a significant fluorescing volume, i.e., a substantial thickness, 1 millimeter, far exceeding the depth of field (Notably, for a spot size of 5 or 1 ½ micron, the depth of field is typically about 50 micron and 4.5 micron, respectively, and progressively less for smaller spot sizes). The fluorescent radiation emitted from this volume causes focus to be difficult to define accurately and hence is an unsatisfactory standard for many purposes.

Accordingly, there is a need for calibration tools, calibration apparatuses, methods and tools used in microscopy.

SUMMARY OF THE INVENTION

The present invention relates to calibration apparatuses, methods and tools used in microscopy. The present invention may separately be used for calibrating a location of a sample with respect to optical elements and for calibrating fluorescence detection in microscopes.

According to one aspect, a calibration tool for fluorescent microscopy includes a support, a solid surface layer including a fluorescent material, and a thin opaque mask of non-fluorescent material defining reference feature openings having selected dimensions exposing portions of the surface layer.

Preferably, a first type of the calibration tool may include an adhesion promoter facilitating contact between the surface of the support and the solid surface layer including the fluorescent material, which is in contact with the thin opaque mask. Alternatively, a second type of the calibration tool may include the thin opaque mask fabricated (with or without an adhesion promoter) onto the support, and the solid surface layer including the fluorescent material located on the thin opaque mask.

Preferred embodiments of this aspect may include one or more of the following: The thin opaque mask is fabricated onto the support using an adhesion promoter. The support is flat and rigid. The support includes fused quartz. The surface layer is opaque. The mask comprises a thin metal film. The support forms an optical window of a cassette. Several suitable types of cassettes are described in U.S. Pat. No. 6,140,044, which is incorporated by refrence.

The fluorophores are excitable by optical radiation passing through the support and/or through the openings in the mask. The fluorophores are excited by optical radiation passing through the support and through the openings in the mask and the support absorbs excited fluorescent radiation. The solid surface layer provides a broadband fluorescence emitter. The solid surface layer provides a fluorescence emitter active at at least two wavelengths and having emission, characteristics similar to Cy3 and Cy5 fluorescent dies. The solid surface layer provides a fluorescence emitter having effective fluorescent emittance that can produce a full scale response for microscope calibration. The solid surface layer including the fluorescent material has a thickness in the range of about 2 micron to about 250 micron. The solid surface layer is polyimide.

The thin opaque mask has a thickness in the range of about 10 nm to about 10 micron. The thin opaque mask has a thickness in the range of about 10 nm to about 100 nm.

According to another aspect, a process for producing a calibration tool for fluorescent microscopy includes providing a support, providing a solid surface layer including a fluorescent material, and fabricating a thin opaque mask of non-fluorescent material defining reference feature openings having selected dimensions exposing portions of the surface layer.

Preferred embodiments of this aspect may include one or more of the following: The solid surface layer may be deposited onto the support the solid surface layer having the fluorescent material. This may include depositing an adhesion promoting layer onto the support for forming the solid surface layer including the fluorescent material. The deposition includes delivering vapor forming the solid surface layer including the fluorescent material, such as evaporating or sputtering. The depositing includes spin coating to form the solid surface layer including the fluorescent material.

The fabrication of the thin opaque mask includes depositing onto the support the non-fluorescent material and patterning the non-fluorescent material to form the reference feature openings. Then, the solid surface layer including the fluorescent material is deposited onto the thin opaque mask.

The support may be fused quartz. The thin opaque mask may include metal. The support may be used as an optical window for a cassette used in examination of biological material.

The solid surface layer provides a broadband fluorescence emitter.

The solid surface layer provides a fluorescence emitter active at at least two wavelengths and having emission characteristics similar to Cy3 and Cy5 fluorescent dyes.

According to another aspect, a method of calibrating a microscope includes providing a microscope, employing the above-described calibration tool, bringing in focus an excitation beam emitted from an objective of the microscope by examining the reference feature opening, and calibrating detection intensity of the microscope. The bringing in focus may include adjusting a position of a sample table wherein the calibration tool is located. The microscope may be an on-axis flying objective microscope. The microscope has a micro-lens objective carried upon an oscillating rotary arm.

The calibration tool is suitable for use with a confocal microscope having a restricted depth of field and the solid surface layer that comprises fluorophores has an effective depth of less than the depth of field of the confocal microscope, preferably the surface layer having an effective fluorescent emittance that can produce a full scale response of the microscope.

According to yet another aspect, a method of quantified fluorescence microscopy includes providing a fluorescence detecting microscope, employing a calibration tool as described above to calibrate the microscope, and performing fluorescence microscopy of specimens employing the calibrated microscope. Preferably the microscope is an on-axis flying objective microscope, and most preferably, the microscope has a micro objective lens carried upon a rapidly oscillating rotary arm.

In a preferred embodiment, a fluorescent calibration tool is built with a suitably fluorescent solid surface layer of constant thickness that is opaque, made of organic material or inorganic material, carried on a suitable support. For materials that are not naturally opaque, dyes or pigments are added. A very thin metal layer is subsequently deposited on the opaque fluorescent material and covered with a layer of photo-resist. An appropriate pattern is then imaged on the photo-resist and chemically etched. The resulting fluorescent pattern showing through the etched openings has extremely fine features because the metal layer is as little as a fraction of a micron thick, preferably about 100 to 300 Angstrom thick. The pattern-creating process can be identical to the process used to create integrated circuits. Presently that technology enables the formation of features as narrow as 0.2 micron width lines separated by spaces of the same dimension.

In the calibration tool, the fluorescence is caused to be a surface emission phenomenon, which permits reliable focusing and fluorescence calibration, that can be used as a standard, and enable all instruments to be set to the same standard. Preferably, the calibration tool uses a very stable fluorescing material, that is insensitive to photobleaching.

An important fluorescing material with a broad band of fluorescent response, is a selected polyimide such as Kapton™ available in liquid form and used for spin coating substrates and creating sheets with 1 to 10 micron thickness. A suitable product is available under the trade designation WE-IIII or PI-IIII from H. D. MicroSystems, Wilmington, Del. This material is a polyimide which has as a backbone a high molecular weight polyimic acid precursor comprised of specific aromatic decanydride and an aromatic diamine.

The fluorescing material may preferably be another polyimide product, Probonide 116A, available from Arch Chemicals of Portsmouth, N.H. This material exhibits broad band fluorescence of approximately ¼ the intensity of the H. D. MicroSystems product, that can be satisfactorily used. Alternatively, fluorescing polyimide material is one that is provided to the semiconductor industry as a self-priming, non-photosensitive polyimic acid formulation which becomes a fully stable polyimide coating after thermal curing.

Another material for the surface layer, suitable for a specific wavelength of interest, is an extremely thin layer of fluorescent glass deposited e.g. by evaporation or by a sol-gel process on a non-fluorescent support. In the case of a sol gel, large molecules of a glassy type of material are suspended, with selected fluorophores in a water or alcohol carrier, and applied as a film coating to a support. It is baked at a relatively low temperature to form a thin glassy fluorescent film. In these and other cases, fluorescing dyes for specific wavelengths are incorporated in a suitable non-fluorescing and preferably opaque binder, applied as a thin, uniform thickness coating. Examples of fluorescing dyes are Cy3, Cy5, and fluorescene.

In all events, the substance of the surface layer must be selected to produce sufficient fluorescence to be detected in the way that is normal to use in, operating the instruments for examining fluorescent specimens. The specific selection of a fluorescing reference material is dependent upon numerous parameters such as the response of the instrument, the selected wavelength, the size of the features to be examined and the spot size of the excitation beam. In the case of the commercial instrument as described as an example in the accompanying appendix, the fluorescent material must produce of the order of one million times the radiation detected at the detector. The polyimide materials described above provide a great benefit over others in being broad band and hence suitable as a single reference that is useful over a range of selected wavelengths at which important experiments are performed.

Some fluorescent microscopy applications demand that the material under inspection be located behind a transparent protective window, typically made of non-fluorescent optical glass such as synthetic quartz. In such cases the alignment tool preferably duplicates the application and the metalized target is first created on the glass and the fluorescent media is applied as a coating covering the metalization as well as the glass, or is provided as a planar coating on a second optically flat member which is then mounted face-to-face with the metal layer on the first optically flat member.

Importantly, in many cases, the effective fluorophores for producing photons that reach the detector lie substantially only in a surface layer. (As used herein, the term, "effective fluorophores" is meant to include substantially all of those fluorophores which are effective to produce meaningful fluorescent radiation from the face of the surface layer that can reach the detector of a microscope, and does not refer to fluorophores which are either out of the range of excitation radiation of the microscope due to the opacity of the matrix, or, though within the range of effective excitation radiation, do not produce fluorescent radiation that reaches the detector of the microscope, due, e.g., to absorption by the opaque matrix material.) The surface fluorophores approximate what occurs when dots of biological specimen material only a fraction of a micron thick produce fluorescence in response to an incident excitation beam.

In the persent calibration tool, limitation of fluorescence to the surface layer suitable for a given application may accomplished by one or a combination of techniques. In one case, the binder material for forming the solid matrix in which the calibration fluorophores are contained, is made essentially opaque at the excitation or detection wavelength or both, such that a large fraction, e.g. 80% or more, preferably as much as 99% of the detected fluorescing radiation, emanates from a surface layer of depth, $\Delta_r$, that is only of the order of the thickness of the specimen to be inspected, and within the depth of field of the instrument. In another case, the micro thickness of a layer in which the fluorophores are confined is controlled to a high degree of uniformity, the layer sitting on an opaque support devoid of fluorophores, such that even if some fluorescence occurs from a depth beyond the preferred bound, the resulting fraction of luminescence outside of the bound is uniform across the tool because of the uniformity of coating thickness, and hence is not effective to significantly disturb the calibration.

In another case, the fluorophores are introduced to a surface layer after preforming the surface layer, e.g., by diffusion, spray or implantation techniques that confine the fluorophores essentially to the surface that is to be exposed by openings in the pattern. Thus, in the calibration tool, an effective solid fluorescent surface layer is provided that can serve as a proxy for the specimen to be examined.

The thickness of the thin metal layer or other material forming the reference pattern also matters, because many rays of the detected fluorescence form an angle as great as 45 degrees with the surface being examined, and can be blocked by the edge walls of the pattern elements, if the elements are too thick, to impair the resolution of detection of the pattern edge. The finer the features to be inspected, the finer must be the calibration of the instrument, hence the more critical becomes the thickness of the pattern elements, i.e., the reference lines, circles, etc., included in the thin opaque mask.

An important aspect is the fluorescent wavelength produced by the fluorescing surface layer. Preferably, the calibration tool is made employing a broad band fluorescent material and thus is useful with various lasers and wavelengths used in a microscopes and with different types of fluorophores used in various lines of scientific or industrial inquiry. In one example, a polyimide material is selected which has effective fluorescence for use as a reference at wavelengths from 473 nm to 850 nm, or more preferably from 450 nm to 800 nm, covering essentially the entire visible spectrum. (The visible spectrum is important, since a great deal of historical biological data has been generated in that region, and is available for reference and comparison as research proceeds.) However, fluorophores in the near infrared and ultraviolet may be employed, given suitable circumstances with respect to the biology and the available sources of illumination and detection.

According to another aspect, the calibration tool is used in combination with a flying objective, on-axis scanner, to achieve highly reproducible quantified fluorescence microscopy. While microscopes with any means of moving the lens preferably a micro lens, is included, significant further advantages are obtainable by employing an oscillating rotary arm to transport the micro lens over the specimen or calibration tool. The calibration of fluorescence detection microscopes, to the calibration of on-axis, wide field of view scanning fluorescence microscopes, and ultimately to quantified fluorescent microscopy having application from the forefront of genomic research and drug discovery to clinical use. The invention has particular application to the accurate reading of biochips and micro arrays.

DESCRIPTION OF THE DRAWINGS

FIG. 1 is a plan view of an alignment tool used in microscopy.

FIG. 2 is a cross-section of the tool taken through certain alignment features along lines 2—2 of FIG. 1.

FIG. 5 illustrates diagramatically another method for fabrication an alignment tool, while

FIG. 5b illustrates diagramatically another method for fabrication an alignment tool, while

DETAILED DESCRIPTION OF PREFERRED EMBODIMENTS

Referring to FIGS. 1 and 2, the alignment tool 2a comprises a generally planar rigid member carrying on its face a detailed pattern of optical features suitable for calibration of the instrument. The rigid member is typically of the same dimensions as the microscope slide, microarray chip or other object to be examined, to fit in the same position on the instrument. The optical features of the alignment tool include lines and circular dots of various dimensions to emulate the various sizes of dots and linear features of biological or other material to be examined. The finest features have dimensions of the order of 1 micron or less to suitably calibrate for detection of features of a few micron dimensions or less.

The calibration tool shown in FIGS. 1 and 2 includes regions T-1, T-2, T-3, T-4, and T-5. Region T-1 includes a set of "barcode" lines having thickness 2 micron, 4 micron, 6 micron, 8 micron, 10 micron, and 12 micron, separated by twice their size. Region T-2 include a long 5 micron and 10 micron line across. Region T-3 includes a solid layer of the fluorescing material. Region T-4 includes three arrays of circular features having diameters from 300 micron to 25 micron, and squares having sizes from 300 micron to 25 micron. Region T-5 is a solid metallic area.

Figure 3:
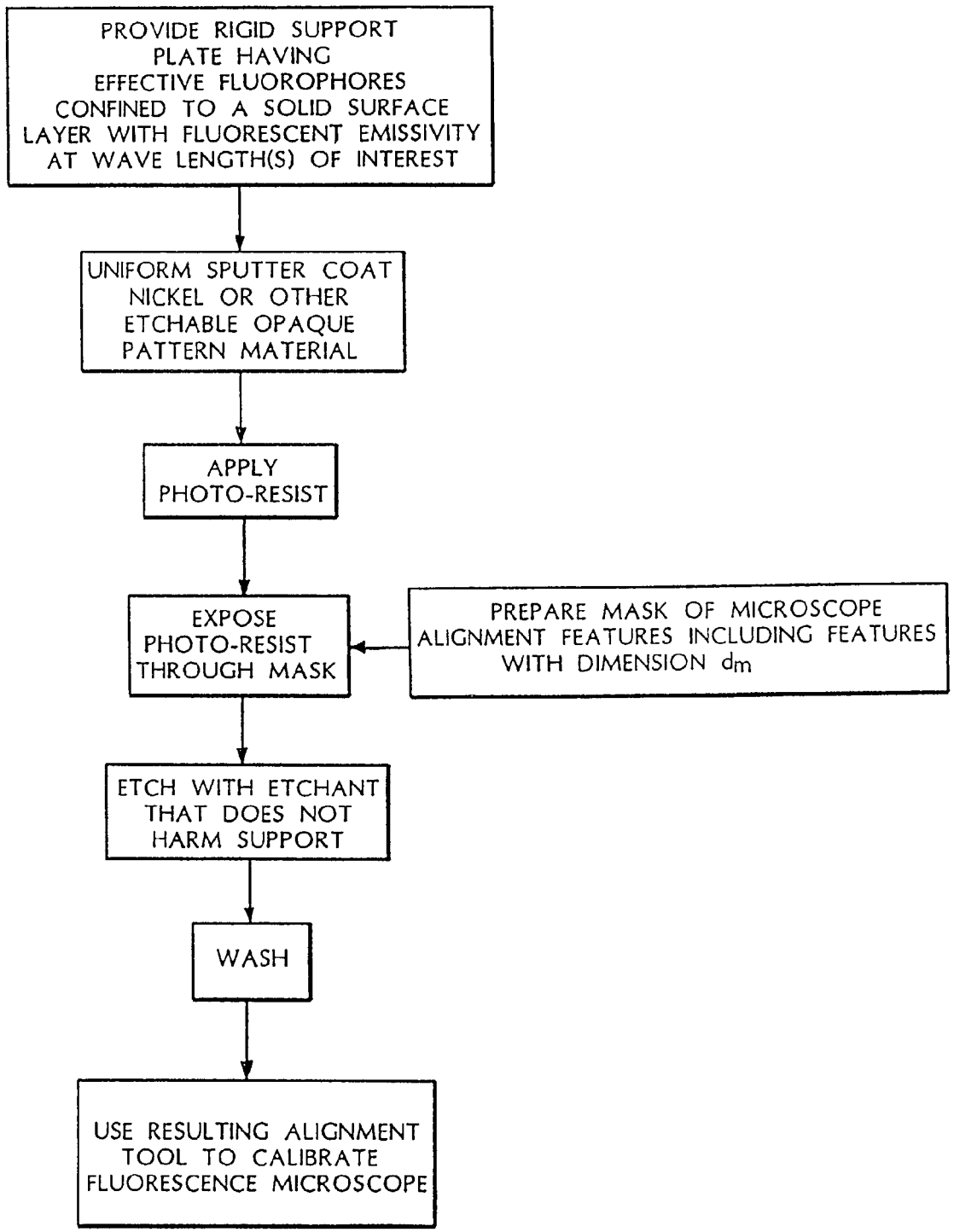
FIG. 3 is a diagram depicting the fabrication of the alignment tool of FIG. 1.

Referring to FIG. 3, in one preferred embodiment the first step in manufacture of the calibration tool is to provide a rigid support plate having effective fluorophores confined to a solid surface layer 4 of only an incremental thickness, see FIG. 2. Typically this depth, delta$_t$, is negligible such that fluorescent emission occurs essentially as a surface phenomenon. Upon this layer, step two, a nickel or other suitable very thin and opaque metal film is applied that is etchable to form a reference pattern. Sputter coating, vacuum metal deposition or other known techniques may be employed. A photo-resist is then applied in general to the metal layer, the photoresist on the tool preform is exposed through a precision mask defining the alignment features and then the surface is chemically etched to form the resulting reference pattern. The resultant tool is used to calibrate fluorescence measurements as well as the conventional image components of fluorescent microscopes.

Figure 4:
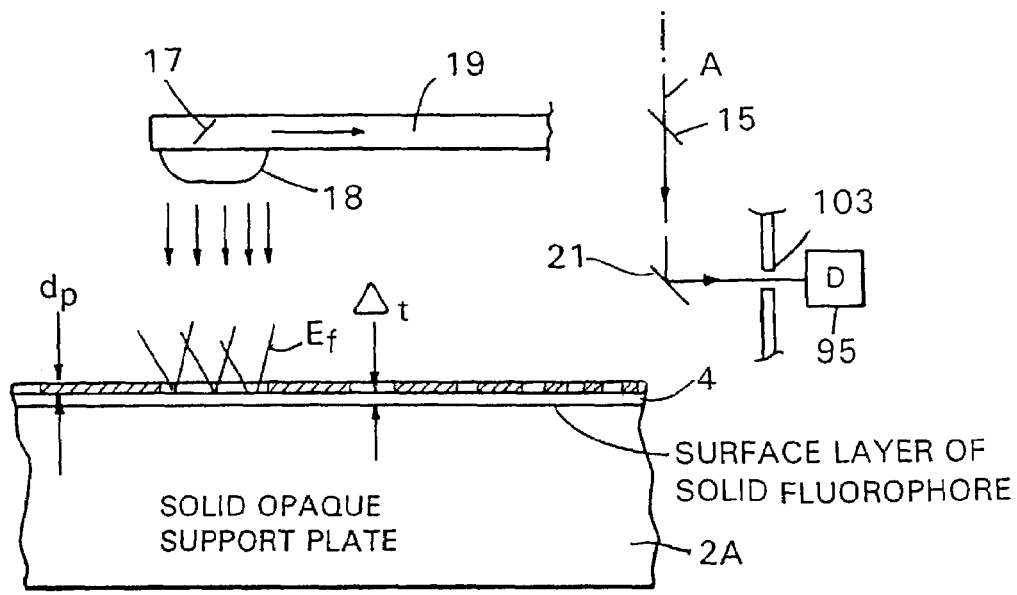
FIG. 4 shows one embodiment of the allignment tool used with a microscope.

Referring to FIG. 4, an oscillating arm 19, rotating about axis A, carries an on-axis micro objective lens 18 for on-axis scanning over the alignment tool 2A which is positioned in the place ordinarily occupied by specimens to be examined. Mirrors 15 and 17 are effective to introduce excitation light from a stationary laser source, along axis of rotation A, thence out along the arm to lens 18, thence to the specimen (or in this case, to the calibration tool). Light reaching the surface layer 4 of the tool excites effective fluorophores, which emanate in all directions at a different wavelength. A significant feature is that this radiation is captured by micro lens 18 (whose axis is always perpendicular to the object plane), and directed back through the optical path and through a restriction such as a pin hole 103, to detector D, 95, typically a photo multiplier tube (PMT).

In the case of FIG. 4, the surface layer 4 is a separately applied layer of uniform minimum thickness applied to a solid, optically flat, opaque support plate. Preferably surface layer 4 is also opaque such that excited light does not substantially penetrate even the surface layer; but even if it does penetrate to a degree, because of the great uniformity of the layer, and the non-emitting character of its support, any incidental fluorescence from below the surface layer$\Delta_t$ is uniform throughout, hence its disturbing effect can in many instances be tolerated. Depending upon the particular instrument and application, in some cases, in which the solid surface layer is extremely thin and sufficiently uniform in thickness and distribution of fluorophore, the surface layer need not be opaque and will still function appropriately to produce essentially only surface emissions.

Figure 4A:
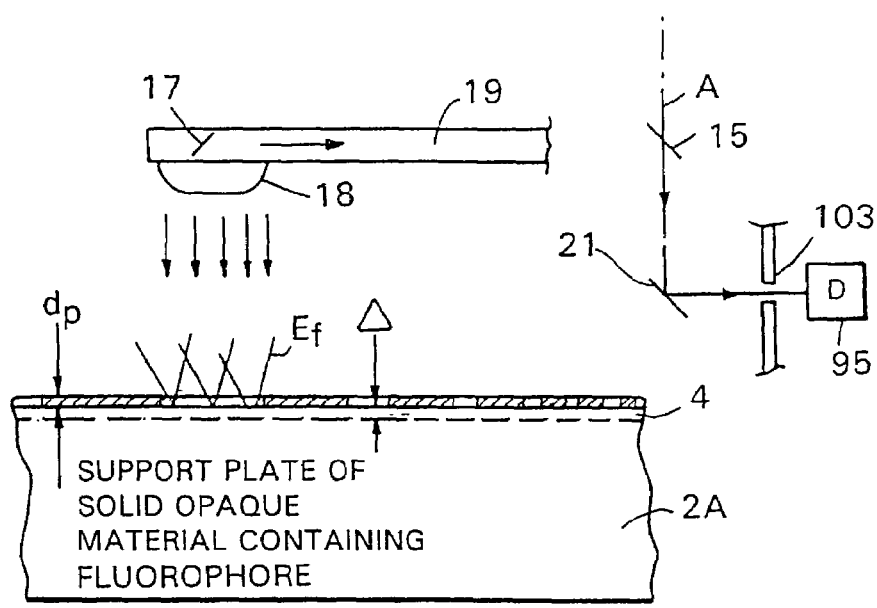
FIG. 4A shows an alternative embodiment of the allignment tool used with a microscope.
Figure 5C:
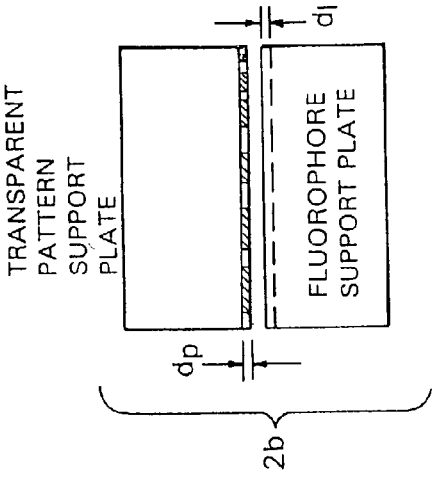
FIGS. 5c and 5d are schematic cross-sectional views of the tool fabrication.
Figure 5:
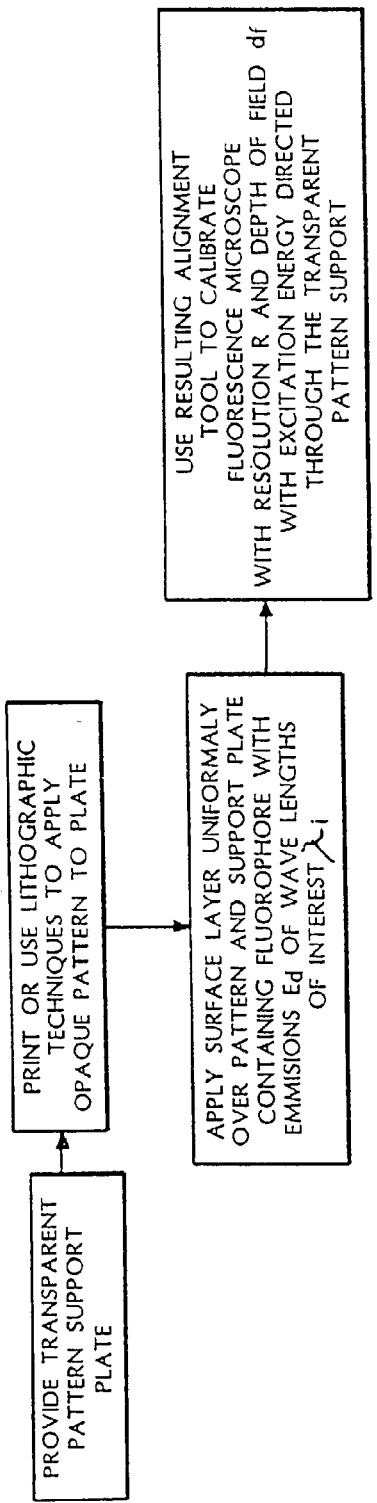
Figure 5A:
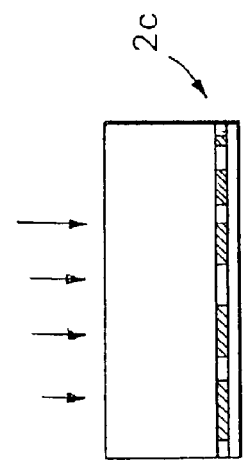
FIG. 5a shows the resulting tool.
Figure 5B:
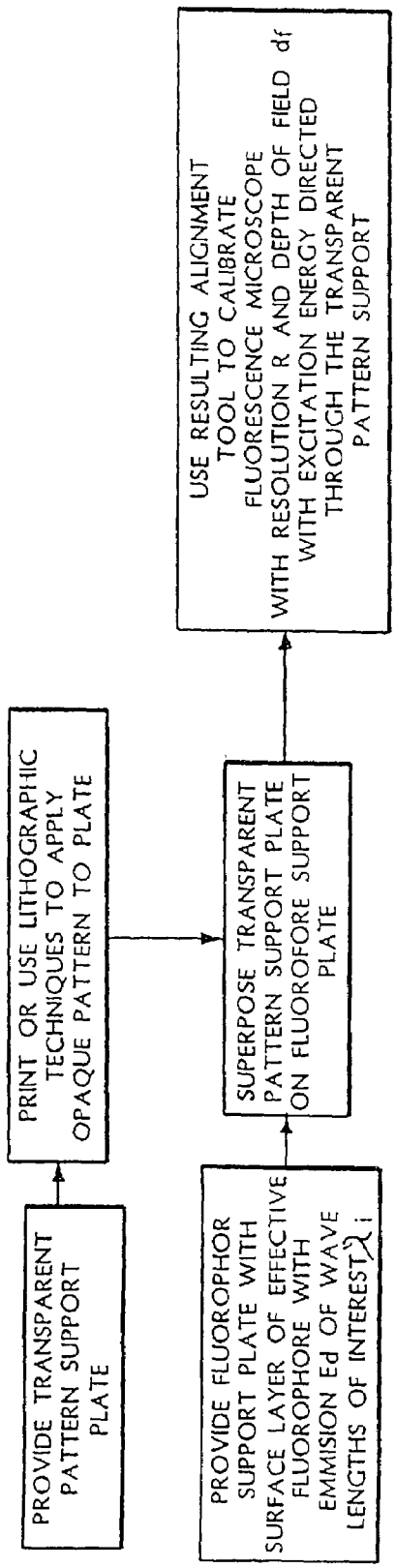
Figure 6:
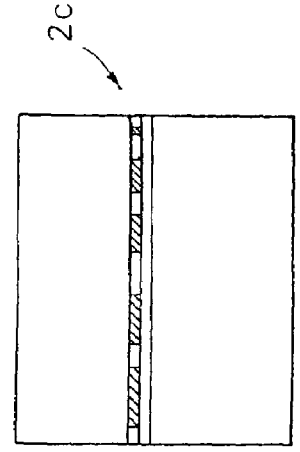
FIG. 6 is a view of an alternative to the construction of the tool shown in FIG. 5B.
Figure 5D:
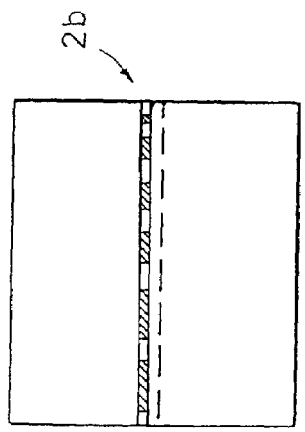
Figure 7:
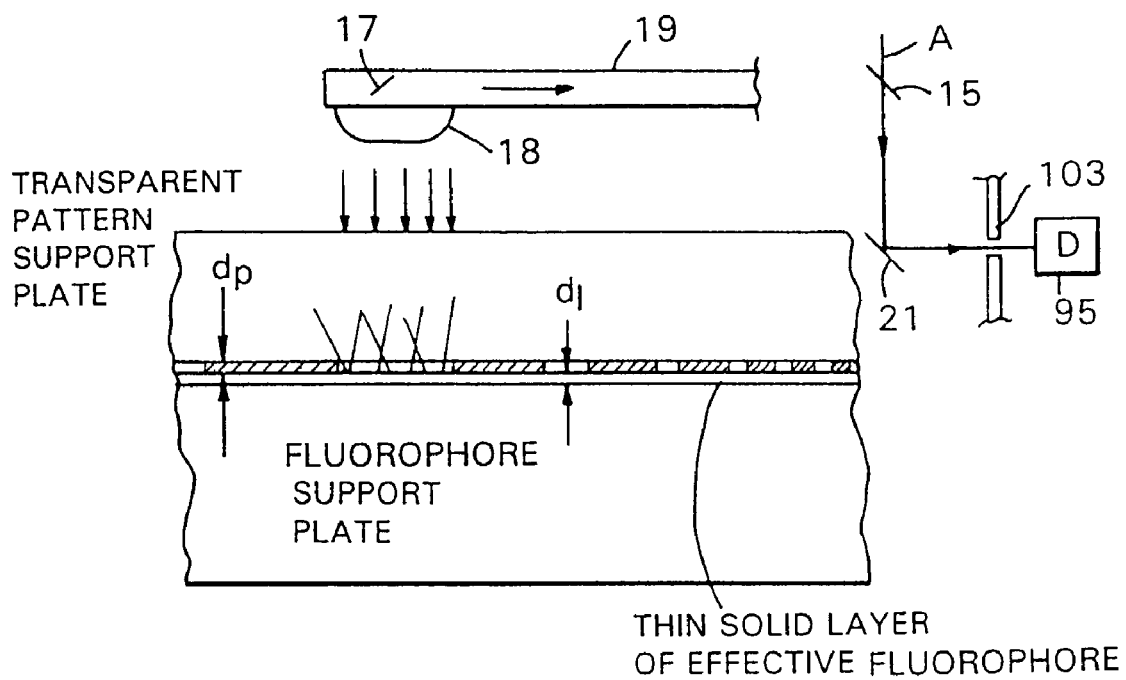
FIG. 7 illustrates the use of the tool shown in FIGS. 5B or 6.

The alternative processes of FIGS. 5 and 5b are self explanatory, both producing calibration tools which, in use, are illuminated by light passing through the transparent pattern support. The tool of FIG. 5A is produced by the steps of FIG. 5 while the tools of FIGS. 5D and 6 are produced employing the steps of FIG. 5B. The tools of FIGS. 5D and 6 differ from each other in the same respect that tools of FIGS. 4 and 4A differ, described above.

Figure 8:
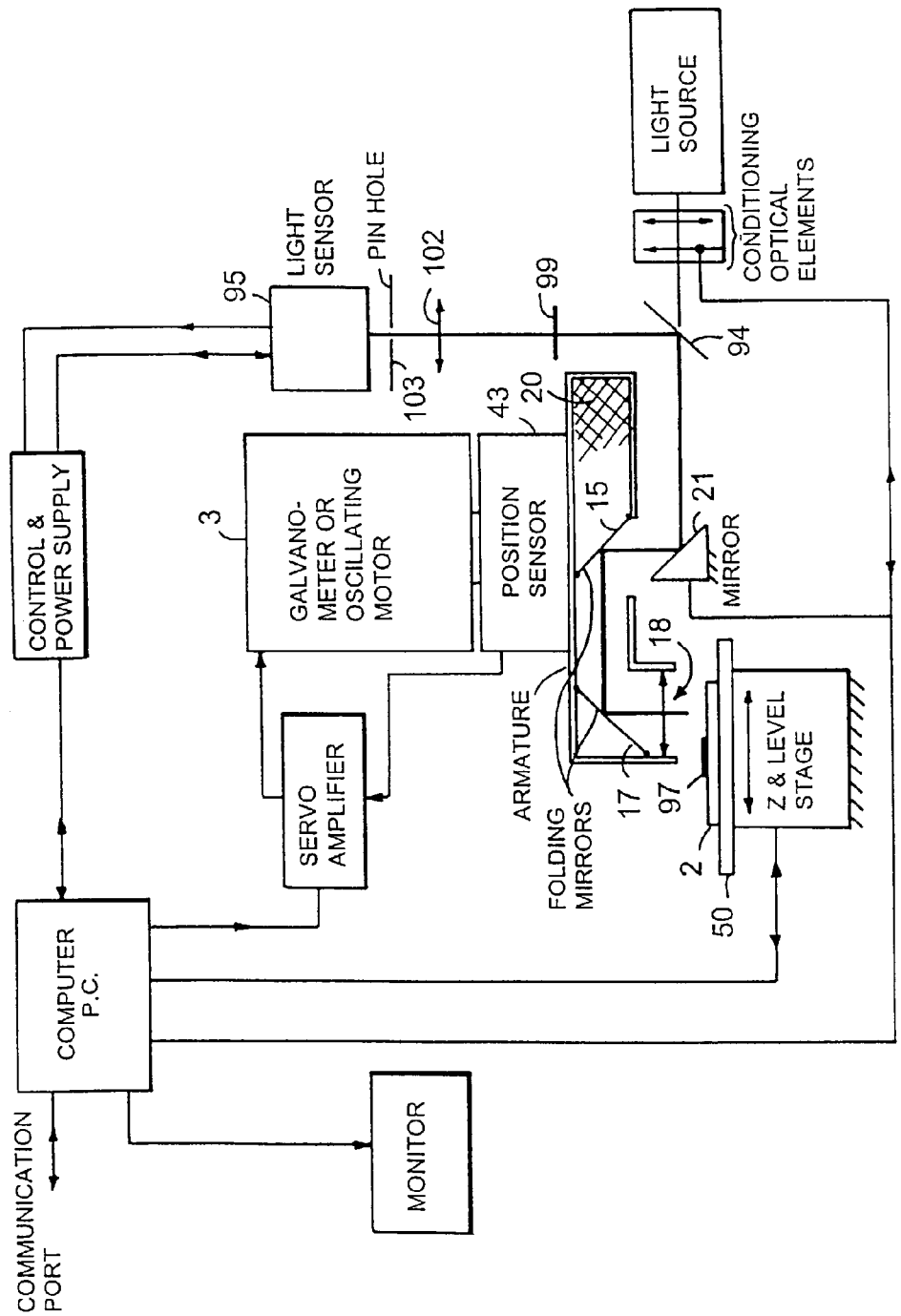
FIGS. 8 and 8A illustrate diagrammatically a wide-angle fluorescent scanning microscope employing a flying micro objective lens on a rapidly rotating, oscillating arm.
Figure 8A:
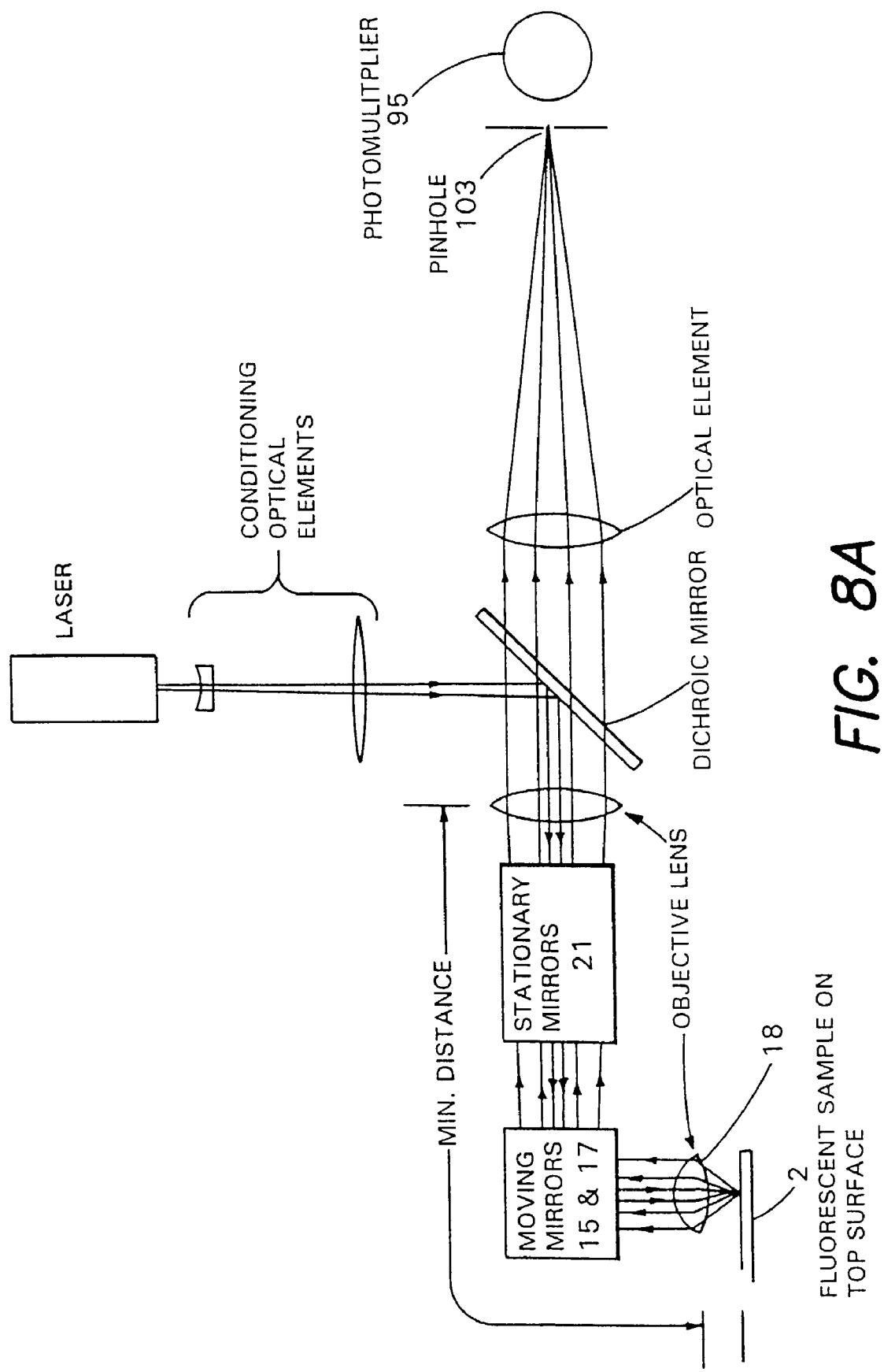
Figure 9:
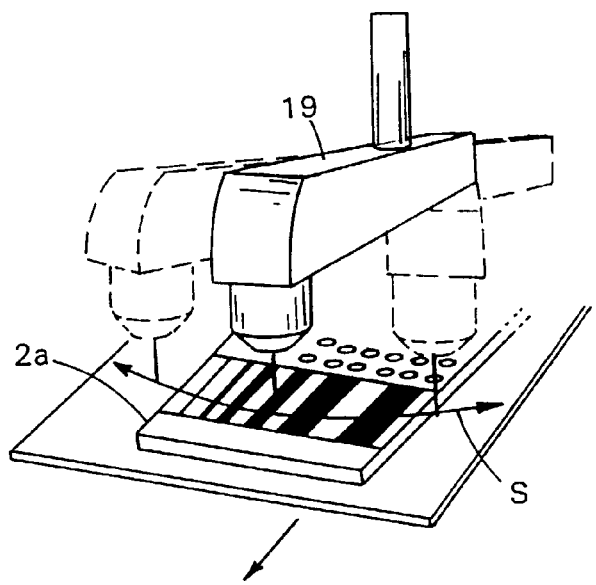
FIG. 9 is a perspective representation of an oscillating arm of the scanning microscope shown in FIG. 8 employing an alignment tool.

The resultant tools are effective to enable standardization of wide field of view fluorescent scanning microscopes such as the microscope depicted in FIGS. 8 and 9. This microscope is described in detail in PCT Application PCT/US99/06097, published as WO99/47964, entitled "Wide Field of View and High Speed Scanning Microscopy," which is hereby incorporated by reference as if fully set forth herein. It is sufficient to say that the micro objective lens 18, mounted on a rotary arm 19 for on-axis scanning, is driven in rapid rotary oscillation movement by galvanometer or oscillating motor 3, whose position is detected by position sensor 43 for the purpose of relating data acquisition to position on the specimen. By employing a pin hole or other restriction 103 in front of the light sensor 95, the resulting confocal microscope has a significantly limited depth of field, which could not be calibrated well by prior techniques but which can be readily calibrated to high accuracy using calibration tools featuring broad band surface emission by fluorescence as has been described here.

Figure 10:
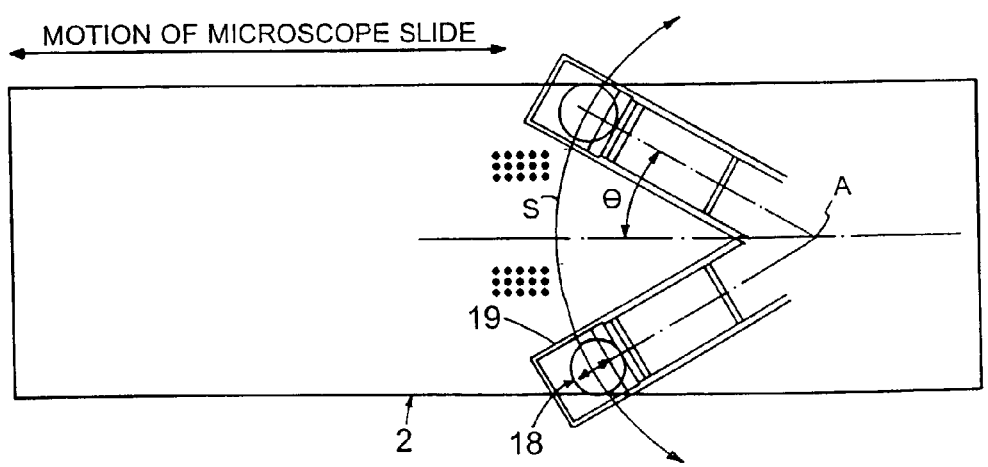
FIG. 10 is a diagramatic plan view of the oscillating arm shown in FIG. 9 used for scanning a microarray of biological material on a glass slide or biochip following the calibration of the scanning microscope shown in FIG. 9.

FIG. 9 depicts employing a calibration tool as described above with a flying objective microscope, whereas FIG. 10 depicts the subsequent scanning of a microarray using the same instrument, now calibrated, to achieve quantified fluorescence microscopy that can readily be compared to the results produced by other microscopes that have been calibrated in the same way.

A rudimentary analysis of the amount of fluorescence required to stimulate an actual specimen is presented in the following appendix with respect to a commercial confocal fluorescence scanning microscope, based on a microlens carried on a rapidly oscillating arm, the 418 Array Scanner™, available from Genetic MicroSystems, Inc. By following a similar analysis for other instruments one can arrive at suitable fluorescent levels for those instruments; by considering the sets of data for all instruments a standard calibration tool is obtainable.

Appendix

Analysis of Fluorescence Required for a Practical Wide Field of View

Flying Objective Microscope with On-Axis Scanning (418 Array Scanner Available from Genetic MicroSystems, Inc.)

TABLE 1

| | |
|---|---|
| (1) Illumination Power: 3 mW on specimen at 6.37 nm | |
| (2) Delivery efficiency to the PMT Detector: | |
| Collection Efficiency: Geometric: 13% | .13 |
| Dichroic Transmission | .9 nm |
| Emission Filter | .6 |
| Approximate Delivery Efficiency to the PMT = | .070 |
| (3) 5 V/nW min Gain of PMT = sensitivity = S | |
| (4) Approximately 0.5 v full scale. Typical PMT signal = C | |
| (5) Assume the weakest PMT is saturated (e.g. Hammamatsu PMT for detection of $\Sigma$ = 637 nm | |
| Response = R = C ÷ S    R = .5 V ÷ 5 V/nw = .1 nw @ PMT    nw S = .1 nW ÷ .070 = 1.4 nW @ microscope slide | |
| (6) Fluorescence Production Rate = 1.4 ($10^{-9}$) ÷ 3 ($10^{-3}$) of the order of 1.5 ÷ 3 ($10^{-6}$) = .5 ($10^{-6}$) | |

In this table, illumination power represents the amount of power that is typically delivered to the microscope slide for exciting fluorescent emission. The delivery efficiency (2) is defined by three values. The first is the geometric collection efficiency of the lens, based upon the size of the confocal pinhole and the distance to the microscope slide. For the instrument of the example, 13% of the fluorescing light emitted is collected, i.e. the fluorescence light is emitted at the target with spherical distribution, and the instrument collects 13% of that light. That light passes through a dichroic mirror, necessarily involving a loss factor, so that 90% of the light is passed and 10% is reflected elsewhere in the system and is wasted. Finally, in front of the photomultiplyer tube an emission filter passes about 60% of the fluorescent light. The emission filter is a multi-layer optical filter which rejects the excitation light that accompanies the fluorescent energy which is generally centered about 25–30 nanometers away from the wavelength of the excitation laser energy.

The model 418 Array Scanner instrument operates at 532 and 637 nanometer. Another useful wavelength is 473 nanometer. At these wavelengths, for this instrument, the surface layer of fluorescing material in the calibration tool must produce fluorescence power leaving its surface of the order of at least 1 millionth the illumination power reaching a specimen.

The product of the three numbers discussed, 0.13×0.9×0.6, shows that the delivery efficiency is approximately 0.070. Referring further to the table, line 3 relates to the gain of the photomultiplyer tube modules employed in the 418 Array Scanner. The modules with the least gain have a gain of 5 volts per nanowatt, meaning typically around 637 nm $\Sigma$, the PMT produces a 5 volt signal for every nanowatt of light reaching it.

At line 4, the 418 Array Scanner system is such that when a full strength signal is obtained, the instrument produces ½ a volt at the photomultiplyer tube.

Thus by assuming that a desired test material will saturate the weakest photomultiplier tube, an equation is produced that shows the desired performance of the material. The response of the photomultiplyer tube is equal to the gain times the signal (amount of light falling on the photomultiplyer tube). This gives a signal equal to ½ volt divided by 5 volts per nanowatt, or 0.1 nanowatts of light are obtained at the photomultiplyer tube. By taking the 0.1 nanowatt and dividing it by the efficiency of 0.07, one determines that at the microscope slide 1.4 nanowatts of fluorescent light are produced, or a little higher. Thus, the fluorescence production rate is approximately 1.4 or $1.5 \times 10^{-9}$ which is the nanowatts divided by $3 \times 10^{-3}$, which is equal to 3 milliwatts. This results in a value of about $\frac{1}{2} \times 10^{-6}$ or a factor of 1 million, meaning that for each fluorescing photon reaching the PMT, approximately 1 million photons are required to impinge on the surface layer of fluorescent material.

This shows that the fluorescent efficiency of the fluorophore needs to be approximately $1 \times 10^{-6}$ or higher. It needs to receive $10^6$ photons for every photon it emits. Accordingly, the conversion efficiency of a suitable fluorescent reference material needs to be of the order of $1 \times 10^{-6}$ or higher.

What is claimed is:

1. A calibration tool for fluorescent microscopy comprising a support, a solid surface layer including a fluorescent material, and a thin opaque mask of non-fluorescent material defining reference feature openings having selected dimensions exposing portions of said surface layer.

2. The calibration tool of claim 1 including an adhesion promoter facilitating contact between a surface of said support and said solid surface layer including said fluorescent material, said solid surface layer being in contact with said thin opaque mask.

3. The calibration tool of claim 1, wherein said thin opaque mask is fabricated onto said support, and wherein said solid surface layer includes the fluorescent material is deposited on said thin opaque mask.

4. The calibration tool of claim 3, wherein said thin opaque mask is fabricated onto said support using an adhesion promoter.

5. The calibration tool of claim 2 or 3 wherein said support is flat and rigid.

6. The calibration tool of claim 2 or 3 wherein said support includes fused quartz.

7. The calibration tool of claim 2 or 3 wherein said mask comprises a thin metal film.

8. The calibration tool of claim 3 wherein said support forms an optical window of a cassette.

9. The calibration tool of claim 3 wherein the fluorescent material includes fluorophores that are excited by optical radiation passing through said support.

10. The calibration tool of claim 3 wherein the fluorescent material includes fluorophores that are excited by optical radiation passing through said support and through said openings in said mask.

11. The calibration tool of claim 3 wherein the fluorescent material includes fluorophores that are excited by optical radiation passing through said support and through said openings in said mask and said support absorbs excited fluorescent radiation.

12. The calibration tool of claim 2 or 3 wherein said solid surface layer including said fluorescent material has a thickness in the range of about 2 $\mu$m to about 250 $\mu$m.

13. The calibration tool of claim 1, 2 or 3 wherein said solid surface layer is polyimide.

14. The calibration tool of claim 2 or 3 wherein said thin opaque mask has a thickness in the range of about 10 nm to about 10 $\mu$m.

15. The calibration tool of claim 14 wherein said thin opaque mask has a thickness in the range of about 10 nm to about 100 nm.

16. The calibration tool of claim 1 wherein said surface layer is opaque.

17. The calibration tool of claim 1 wherein said solid surface layer provides a broadband fluorescence emitter.

18. The calibration tool of claim 1 wherein said solid surface layer provides a fluorescence emitter active at at least two wavelengths and having emission characteristics similar to Cy3 and Cy5 fluorescent dyes.

19. The calibration tool of claim 1 wherein said solid surface layer provides a fluorescence emitter having effective fluorescent emittance that can produce a full scale response for microscope calibration.

20. A process for producing a calibration tool for fluorescent microscopy comprising:
providing a support;
providing a solid surface layer including a fluorescent material; and
fabricating a thin opaque mask of non-fluorescent material defining reference feature openings having selected dimensions exposing portions of said surface layer.

21. The process of claim 20 wherein said providing a solid surface layer includes depositing onto said support said solid surface layer including said fluorescent material.

22. The process of claim 21 including depositing an adhesion promoting layer onto said support for forming said solid surface layer including said fluorescent material.

23. The process of claim 21 wherein said depositing includes delivering vapor forming said solid surface layer including said fluorescent material.

24. The process of claim 23 wherein said delivering vapor includes evaporating material, onto said support, forming said solid surface layer including said fluorescent material.

25. The process of claim 23 wherein said delivering vapor includes sputtering material, onto said support, forming said solid surface layer including said fluorescent material.

26. The process of claim 21 wherein said depositing includes spin coating to form said solid surface layer including said fluorescent material.

27. The process of claim 20 wherein said fabricating said thin opaque mask includes depositing onto said support said non-fluorescent material and patterning said non-fluorescent material to form said reference feature openings.

28. The process of claim 27 wherein said providing a solid surface layer includes depositing said solid surface layer including said fluorescent material onto said thin opaque mask.

29. The process of claim 20, 21 or 27 wherein said support is fused quartz.

30. The process of claim 20, 21 or 27 wherein said thin opaque mask includes metal.

31. The process of claim 27 including using said support as an optical window for a cassette used in examination of biological material.

32. The process of claim 20, 21 or 27 wherein said solid surface layer provides a broadband fluorescence emitter.

33. The process of claim 20, 21 or 27 wherein said solid surface layer provides a fluorescence emitter active at at least two wavelengths and having emission characteristics similar to Cy3 and Cy5 fluorescent dyes.

34. The process of claim 20, 21 or 27 wherein said solid surface layer provides a fluorescence emitter having effective fluorescent emittance that can produce a full scale response for microscope calibration.

35. The process of claim 20, 21 or 27 wherein said solid surface layer including said fluorescent material has a thickness in the range of about 2 $\mu$m to about 250 $\mu$m.

36. The process of claim 20, 21 or 27 wherein said solid surface layer is polyimide.

37. The process of claim 20, 21 or 27 wherein said thin opaque mask has a thickness in the range of about 10 nm to about 10 $\mu$m.

38. The process of claim 37 wherein said thin opaque mask has a thickness in the range of about 10 nm to about 100 nm.

39. A method of calibrating a microscope comprising:
providing a scanning microscope,
providing a calibration tool comprising a support, a solid surface layer including a fluorescent material, and a thin opaque mask of non-fluorescent material defining reference feature openings having selected dimensions exposing portions of said surface layer,
bringing in focus an excitation beam emitted from an objective of said microscope,
examining at least some of said reference feature openings, and
calibrating detection intensity of said microscope.

40. The method of claim 39 wherein said bringing in focus includes adjusting a position of a sample table of scanning microscope where said calibration tool is located.

41. The method of claim 39 wherein said microscope is an on-axis flying objective microscope.

42. The method of claims 41 wherein said microscope has a micro-lens objective carried upon an oscillating rotary arm.

* * * * *